(12) United States Patent
Anthony et al.

(10) Patent No.: US 8,888,736 B2
(45) Date of Patent: *Nov. 18, 2014

(54) HIGH SHEAR APPLICATION IN MEDICAL THERAPY

(75) Inventors: Rayford G. Anthony, College Station, TX (US); Abbas Hassan, Sugar Land, TX (US); Aziz Hassan, Sugar Land, TX (US)

(73) Assignee: H R D Corporation, Houston, TX (US)

( * ) Notice: Subject to any disclaimer, the term of this patent is extended or adjusted under 35 U.S.C. 154(b) by 78 days.

This patent is subject to a terminal disclaimer.

(21) Appl. No.: 13/441,315

(22) Filed: Apr. 6, 2012

(65) Prior Publication Data

US 2013/0096489 A1 Apr. 18, 2013

Related U.S. Application Data

(63) Continuation-in-part of application No. 13/082,882, filed on Apr. 8, 2011.

(60) Provisional application No. 61/355,448, filed on Jun. 16, 2010, provisional application No. 61/330,104, filed on Apr. 30, 2010.

(51) Int. Cl.
| | |
|---|---|
| *A61M 5/00* | (2006.01) |
| *A61M 5/14* | (2006.01) |
| *B01F 7/00* | (2006.01) |
| *B01F 13/10* | (2006.01) |
| *A61K 41/00* | (2006.01) |
| *A61K 9/00* | (2006.01) |
| *A61K 45/06* | (2006.01) |
| *A61K 9/10* | (2006.01) |
| *A61K 31/10* | (2006.01) |
| *A61K 31/198* | (2006.01) |
| *A61K 33/00* | (2006.01) |
| *A61K 33/04* | (2006.01) |
| *A61K 33/40* | (2006.01) |

(52) U.S. Cl.
CPC .......... *A61M 5/1409* (2013.01); *B01F 7/00766* (2013.01); *B01F 13/1016* (2013.01); *A61K 41/0004* (2013.01); *A61K 9/0019* (2013.01); *A61K 9/0029* (2013.01); *A61K 45/06* (2013.01); *A61K 9/10* (2013.01); *A61K 31/10* (2013.01); *A61K 31/198* (2013.01); *A61K 33/00* (2013.01); *A61K 33/04* (2013.01); *A61K 33/40* (2013.01); *A61M 5/1407* (2013.01); *A61M 5/1408* (2013.01); *A61M 2202/0208* (2013.01); *A61M 2202/0216* (2013.01); *A61M 2202/0233* (2013.01); *A61M 2202/0241* (2013.01); *A61M 2202/0266* (2013.01); *A61M 2205/36* (2013.01); *A61M 2206/16* (2013.01); *A61M 2206/20* (2013.01)
USPC ............................................ 604/24; 424/400

(58) Field of Classification Search
None
See application file for complete search history.

(56) References Cited

U.S. PATENT DOCUMENTS

| | | | |
|---|---|---|---|
| 3,887,167 | A | 6/1975 | Irwin |
| 5,538,191 | A | 7/1996 | Holl |
| 5,877,350 | A | 3/1999 | Langer et al. |
| 6,333,021 | B1 | 12/2001 | Schneider et al. |
| 6,368,366 | B1 | 4/2002 | Langer et al. |
| 6,368,367 | B1 | 4/2002 | Langer et al. |
| 6,383,237 | B1 | 5/2002 | Langer et al. |
| 6,530,964 | B2 | 3/2003 | Langer et al. |
| 6,742,774 | B2 | 6/2004 | Holl |
| 2003/0043690 | A1 | 3/2003 | Holl |
| 2004/0052158 | A1 | 3/2004 | Holl |
| 2004/0187770 | A1 | 9/2004 | Calabrese et al. |
| 2005/0033069 | A1 | 2/2005 | Holl et al. |
| 2006/0245991 | A1 | 11/2006 | Holl |
| 2007/0160577 | A1 | 7/2007 | Damle et al. |
| 2007/0160658 | A1 | 7/2007 | Connor et al. |
| 2008/0161588 | A1 | 7/2008 | Hassan et al. |
| 2008/0193520 | A1 | 8/2008 | Moschwitzer et al. |
| 2009/0005553 | A1 | 1/2009 | Hassan et al. |
| 2009/0005592 | A1 | 1/2009 | Hassan et al. |
| 2009/0186088 | A1 | 7/2009 | Chan et al. |

(Continued)

FOREIGN PATENT DOCUMENTS

| | | |
|---|---|---|
| CN | 101068531 | 11/2007 |
| CN | 101312713 | 11/2008 |

(Continued)

OTHER PUBLICATIONS

Stride et al., Soft Matter, 2008, 4, 2350-2359.*

(Continued)

*Primary Examiner* — Michael G Hartley
*Assistant Examiner* — Robert Cabral
(74) *Attorney, Agent, or Firm* — Timothy S. Westby; Porter Hedges LLP

(57) ABSTRACT

In this disclosure, a method is described wherein the method comprises mixing a therapeutic gas or a therapeutic liquid or a combination thereof and a liquid carrier in a high shear device to produce a dispersion; and administering the produced dispersion intravenously to a patient; wherein the produced dispersion contains nanobubbles of the therapeutic gas or droplets of the therapeutic liquid with a mean diameter of less than about 1.5 μm. In this disclosure, a method is described wherein the method comprises mixing a therapeutic gas or a therapeutic liquid or a combination thereof and a liquid carrier in a high shear device to produce a therapeutic fluid, wherein said therapeutic fluid is a solution, a dispersion, or combination thereof and administering the produced therapeutic fluid intravenously to a patient; wherein the solution is supersaturated with the therapeutic gas, the therapeutic liquid, or combination thereof.

11 Claims, 5 Drawing Sheets

(56) References Cited

U.S. PATENT DOCUMENTS

| | | | |
|---|---|---|---|
| 2010/0008863 | A1 | 1/2010 | Swenson et al. |
| 2010/0029518 | A1 | 2/2010 | Markovitz et al. |
| 2010/0030387 | A1 | 2/2010 | Sen |
| 2010/0035800 | A1 | 2/2010 | Desai et al. |
| 2010/0086490 | A1 | 4/2010 | Allemann et al. |
| 2010/0324308 | A1 | 12/2010 | Hassan et al. |
| 2011/0229555 | A1* | 9/2011 | Helson et al. ............... 424/450 |
| 2012/0070475 | A1* | 3/2012 | Zhang et al. ............... 424/400 |

FOREIGN PATENT DOCUMENTS

| | | |
|---|---|---|
| JP | 61500432 | 3/1986 |
| JP | 2003160477 | 6/2003 |
| JP | 2005509596 | 4/2005 |
| JP | 2006306879 | 11/2006 |
| WO | 0154663 | 8/2001 |
| WO | 02064708 A2 | 8/2002 |
| WO | 03013474 | 2/2003 |
| WO | 2004064769 | 8/2004 |
| WO | 2006029845 | 3/2006 |
| WO | 2008070538 | 6/2008 |
| WO | 2009002766 | 12/2008 |
| WO | 2009003031 | 12/2008 |
| WO | 2010039970 | 4/2010 |
| WO | 2010085607 | 7/2010 |

OTHER PUBLICATIONS

Japanese Office Action dated Oct. 29, 2013 for Japanese Application No. 2013-506170 (1 pg.).
Office Action dated Dec. 5, 2013 for corresponding U.S. Appl. No. 13/082,882 (12 pgs.).
Japanese Office Action dated Dec. 10, 2013 for Japanese Application No. 2013-506171 (3 pgs.).
Canadian Office Action dated Nov. 18, 2013 for Canadian Application No. 2,797,913 (2 pgs.).
Chinese Office Action dated Dec. 10, 2013 for Chinese Application No. 201180021897.0 (14 pgs.).
Australian Examination Report Action dated Feb. 20, 2014 for Australian Application No. 2011248866 (3 pgs.).
IKA, "Introduction to IKA's Three Stage Dispax Reactor," Retrieved from <http://www.ikausa.com/pdfs/process/dr%202000-Homogenizing-Dispersing-Suspending-Emulsifying.pdf> on Aug. 22, 2012 (12 pgs.).
International Preliminary Report on Patentability dated Nov. 6, 2012 for corresponding International Application No. PCT/US2011/031727 (5 pgs.).
Junghanns et al., "Nanocrystal Technology, Drug Delivery and Clinical Applications," International Journal of Nanomedicine, dated 2008, vol. 3, No. 3, pp. 295-309 (16 pgs.).
Office Action dated Feb. 12, 2013 for corresponding U.S. Appl. No. 13/082,905 (19 pgs.).
Office Action dated Jul. 28, 2010 for corresponding U.S. Appl. No. 12/635,433 (12 pgs.).
Office Action dated Apr. 20, 2010 for corresponding U.S. Appl. No. 12/427,286 (17 pgs.).
Office Action dated Apr. 23, 2010 for corresponding U.S. Appl. No. 12/568,155 (19 pgs.).
Office Action dated Apr. 27, 2010 for corresponding U.S. Appl. No. 12/568,280 (17 pgs.).
Office Action dated May 5, 2010 for corresponding U.S. Appl. No. 12/142,120 (16 pgs.).
Office Action dated Apr. 20, 2010 for corresponding U.S. Appl. No. 12/411,660 (14 pgs.).
Australian Office Action dated Apr. 22, 2013 for corresponding Australian Application No. 2011248867 (4 pgs.).
Japan Office Action dated Oct. 1, 2014 for corresponding Japanese Application No. 2013-506170 (3 pgs.).
Chattopadhyay et al., "Understanding Mechanical Energy Driven Nonequilibrium Processing: Some Results, Eleventh International Conference on Rapidly Quenched and Metastable Materials," A Material Science and Engineering, vol. 375-377, dated Jul. 15, 2004, pp. 72-77 (9 pgs.).
Australian Examination Report dated Jul. 1, 2014 for corresponding Australian Application No. 2011248867 (4 pgs.).
Canadian Office Action dated Aug. 7, 2013 for corresponding Canadian Application No. 2,798,049 (2 pgs.).
Notice of Allowance dated Oct. 18, 2013 for U.S. Appl. No. 13/082,905 (21 pgs.).
Japanese Office Action dated Oct. 29, 2013 for Japanese Application No. 2013-506170 (2 pgs.).
Indonesian Office Action dated Aug. 4, 2014 for corresponding Indonesian Application No. W00201203993 (2 pgs.).
Chinese Office Action dated Aug. 7, 2014 for corresponding Chinese Application No. 201180021836.4 (8 pgs.).
Chinese Office Action dated Aug. 18, 2014 for corresponding Chinese Application No. 201180021897.0 (20 pgs.).
Australian Office Action dated Sep. 11, 2014 for corresponding Australian Application No. 2011248867 (7 pgs.).
Canadian Office Action dated May 30, 2014 for corresponding Canadian Application No. 2,798,049 (2 pgs.).
Geng et al., "Hydrogen Sulfide: a Novel Cardiovascular Functional Regulatory Gas Factor," Journal of Peking University (Health Sciences); vol. 36; No. 1; p. 106; dated Feb. 2004 (1 pg.).
Zhang et al., "Medical Application of Hydrogen Molecule: Recent Progress," Academic Journal of Second Military Medical University; vol. 30; No. 10; pp. 1203-1205; dated Oct. 2009 (3 pgs.).
Chen Qiotig-yang, "Application of Medical Gases in the Medical," Hunan Agricultural Machinery; vol. 36; No. 3; pp. 32-34; dated May 31, 2009 (3 pgs.).
Yan et al., "Recent Advances in Research of Garlic's Chemical Constituents and Theirs Pharmacological Effects," Chinese Journal of New Drugs; vol. 13; No. 8; pp. 688-691; dated Dec. 31, 2004 (4 pgs.).
Eurasian Office Action dated Sep. 2, 2014 for corresponding Eurasian Application No. 201291018/13 (3 pgs.).
Office Action dated Jun. 3, 2011 for U.S. Appl. No. 12/568,280 (16 pgs.).
Office Action dated Jun. 2, 2011 for U.S. Appl. No. 12/427,286 (12 pgs.).
Office Action dated Jun. 25, 2009 for U.S. Appl. No. 12/142,447 (10 pgs.).
Office Action dated Jan. 7, 2010 for U.S. Appl. No. 12/142,447 (6 pgs.).
Office Action dated May 13, 2010 for U.S. Appl. No. 12/142,447 (5 pgs.).
Office Action dated Feb. 4, 2010 for U.S. Appl. No. 12/492,721 (5 pgs.).
Office Action dated Feb. 18, 2010 for U.S. Appl. No. 12/635,433 (6 pgs.).
Office Action dated Feb. 18, 2010 for U.S. Appl. No. 12/635,454 (6 pgs.).
Office Action dated May 14, 2010 for U.S. Appl. No. 12/137,441 (15 pgs.).
Office Action dated Feb. 19, 2010 for U.S. Appl. No. 12/144,459 (10 pgs.).
Office Action dated Sep. 2, 2009 for U.S. Appl. No. 12/142,433 (11 pgs.).
Office Action dated Jan. 29, 2010 for U.S. Appl. No. 12/142,433 (8 pgs.).
Office Action dated May 24, 2011 for U.S. Appl. No. 12/142,433 (10 pgs.).
Office Action dated Apr. 30, 2010 for U.S. Appl. No. 12/141,191 (12 pgs.).
Office Action dated Oct. 27, 2009 for U.S. Appl. No. 12/142,120 (15 pgs.).
Office Action dated May 5, 2010 for U.S. Appl. No. 12/571,537 (12 pgs.).
Office Action dated Feb. 24, 2011 for U.S. Appl. No. 12/796,358 (13 pgs.).
Office Action dated Feb. 29, 2012 for U.S. Appl. No. 12/146,733 (8 pgs.).
Office Action dated Jun. 3, 2011 for U.S. Appl. No. 12/568,155 (11 pgs.).

(56) References Cited

OTHER PUBLICATIONS

Australian Examination Report dated Feb. 18, 2013 for corresponding Australian Application No. 2011248866 (3 pgs.).
IKA—Single Stage Shear Pumps: Ultra Turax UTL 2000-2003 Processing Ctalog (2 pgs.).
IKA-DRS Reactors website http://www.ikausa.com/dr.him, on Sep. 8, 2010 (2 pgs.).
"Cavitation: A Technology on the Horizon," Current Science 91 (No. 1): 35-46 (2006).
Benavides et. al., Proceedings of the National Academy of Sciences, vol. 104, No. 46, 17977-17982.
IKA—Rotor Stator Generators—2003 Process Catalog (38 pgs.).
Fox B. Schantz JT et al., Inducible Hydrogen Sulfide Synthesis in Chondrocytes and Mesenchymal Progenitor Cells: Is h(2) S a Novel Cytoprotective Mediator in the inflamed Joint?, J Cell Mol Med. (Jun. 17, 2011) (2 pgs).
Matthew Whiteman et al., "Hydrogen Sulfide and Inflammation: the Good, the Bad, the Ugly and the Promising" Expert Rev. Clin. Pharmacol. 4(1), 13-32 (2011).
PCT Search Report and Written Opinion dated Feb. 8, 2012 for corresponding PCT Application No. PCT/US2011/031725 (9 pgs.).
PCT Search Report and Written Opinion dated Feb. 17, 2012 for corresponding PCT Application No. PCT/US2011/031727 (11 pgs).
Office Action dated Mar. 27, 2014 for corresponding U.S. Appl. No. 13/082,882 (17 pgs.).
Office Action dated Mar. 27, 2014 for corresponding U.S. Appl. No. 14/085,420 (29 pgs.).
Office Action dated Apr. 1, 2014 for corresponding U.S. Appl. No. 14/075,105 (24 pgs.).
Japanese Office Action dated Apr. 1, 2014 for corresponding Japan Application No. 2013-506171 (2 pgs.).
Chinese Office Action dated Feb. 13, 2014 for corresponding Chinese Application No. 201180021836.4 (2 pgs.).
Ho, Dean, "Nanodiamonds [Electronic Resource]: Applications in Biology and Nanoscale Medicine," n.p.: Boston, MA : Springer Science+Business Media, LLC, dated 2010 (47 pgs.).
Indonesian Office Action dated Jun. 14, 2014 for corresponding Indonesian Application No. W00201203993 (2 pgs.).
European Search Report dated May 19, 2014 for corresponding European Application No. 11777787.0-1455 (7 pgs.).
European Search Report dated May 19, 2014 for corresponding European Application No. 11777788.8-1455 (8 pgs).

\* cited by examiner

HIGH SHEAR APPLICATION IN MEDICAL THERAPY

CROSS-REFERENCE TO RELATED APPLICATIONS

This application is a continuation-in-part of U.S. application Ser. No. 13/082,882, filed Apr. 8, 2011, which claims the benefit under 35 U.S.C. §119(e) of U.S. Provisional Patent Application Nos. 61/330,104 filed Apr. 30, 2010, and 61/355,448 filed Jun. 16, 2010, the disclosure of each application is hereby incorporated herein by reference.

STATEMENT REGARDING FEDERALLY SPONSORED RESEARCH OR DEVELOPMENT

Not applicable.

FIELD OF THE INVENTION

The present invention generally relates to treatment of various diseases. More particularly, the present invention relates to utilizing a shear device for treatment of various diseases.

BACKGROUND

Heart disease or cardiovascular diseases is the class of diseases that involve the heart or blood vessels (arteries and veins), which is the No. 1 cause of deaths in the United States. In most countries worldwide, the populations are facing high and increasing rates of cardiovascular diseases. Cancer (i.e., malignant neoplasm), as the No. 2 cause of deaths in the United States, is a class of diseases in which a group of cells display uncontrolled growth (division beyond the normal limits), invasion (intrusion on and destruction of adjacent tissues), and sometimes metastasis (spread to other locations in the body via lymph or blood). Cancer affects people at all ages with the risk for most types increasing with age. Cancer caused about 13% of all human deaths in 2007 (7.6 million). Most cancers are treated by surgery, radiation, chemotherapy, hormones, or immunotherapy. In the area of blood oxygenation, two main types of blood substitutes are in development, hemoglobin-based oxygen carriers (HBOCs) and perfluorocarbon emulsions (PFCs).

Oxidative stress is caused by an imbalance between the production of reactive oxygen species (ROS) and a biological system's ability to readily detoxify the reactive intermediates or easily repair the resulting damage. Reactive oxygen species (ROS) are reactive molecules that contain the oxygen atom. They are very small molecules that include oxygen ions and peroxides and can be either inorganic or organic. They are highly reactive due to the presence of unpaired valence shell electrons. Reactive oxygen species can be beneficial, as they are used by the immune system as a way to attack and kill pathogens. Moreover, ROS form as a natural byproduct of the normal metabolism of oxygen and have important roles in cell signaling. However, during times of environmental stress (e.g., UV or heat exposure) ROS levels can increase dramatically, which can result in significant damage to cell structures. This cumulates into the oxidative stress situation. ROS are also generated by exogenous sources such as ionizing radiation.

Reactive oxygen species are implicated in cellular activity to a variety of inflammatory responses including cardiovascular disease. They may also be involved in hearing impairment via cochlear damage induced by elevated sound levels, ototoxicity of drugs such as cisplatin, and in congenital deafness in both animals and humans. Redox signaling is also implicated in mediation of apoptosis or programmed cell death and ischaemic injury. Specific examples include stroke and heart attack. Generally, harmful effects of reactive oxygen species on the cell include DNA and RNA damage, oxidations of polydesaturated fatty acids in lipids (i.e., lipid peroxidation), oxidations of amino acids in proteins, and oxidative inactivation of specific enzymes by oxidation of co-factors.

All forms of life maintain a reducing environment within their cells. This reducing environment is preserved by enzymes that maintain the reduced state through a constant input of metabolic energy. Disturbances in this normal redox (reduction-oxidation reaction) state can cause toxic effects through the production of peroxides and free radicals that damage all components of the cell, including proteins, lipids, and DNA. In humans, oxidative stress is involved in many diseases, such as atherosclerosis, Parkinson's disease, heart failure, myocardial infarction, Alzheimer's disease, fragile X syndrome and chronic fatigue syndrome, but short-term oxidative stress may also be important in prevention of aging by induction of a process named mitohormesis. According to the Free-radical theory, oxidative damage initiated by reactive oxygen species is a major contributor to the functional decline that is characteristic of aging.

Treatment of various diseases (i.e., medical therapy) remains one of the most complex, intriguing, and challenging areas in industry, medicine, research, science, and technology. Therefore there is an ongoing need and interest to develop new methods and systems to improve disease treatment/management in various aspects.

SUMMARY

Embodiments of the present disclosure pertain to a method that may include the steps of mixing one of a therapeutic gas, a therapeutic liquid, or a combination thereof, and a liquid carrier in a high shear device to produce a dispersion; and administering the produced dispersion intravenously to a patient; wherein the produced dispersion may contain nanobubbles of said therapeutic gas or droplets of said therapeutic liquid with a mean diameter of less than about 1.5 µm; wherein said therapeutic gas may be selected from the group consisting of ozone, sulfur based gases, carbon monoxide, oxygen, hydrogen, nitrogen, an anesthetic gas, a noble gas, and mixtures thereof and wherein said therapeutic liquid may be selected from the group consisting of sulfur, a sulfate, an organo metallic, an antibiotic, a steroid, a vitamin, an organosulfur compound, allyl propyl disulfide, diallyl disulfide (DADS or 4,5-dithia-1,7-octadiene), allyl trisulfide (DATS), 5-Allyl cysteine (SAC), a vinyldithiine, a sulfonyl compound, an antioxidant, a lipid, a chelating agent, and combinations thereof.

In an embodiment, the method is utilized to treat coma. In an embodiment, the method is utilized to treat diabetes. In an embodiment, the method is utilized to treat dementia. In an embodiment, the method is utilized to treat Alzheimer's disease. In an embodiment, the method is utilized to treat Parkinson's disease. In an embodiment, the method is utilized to treat high blood pressure. In an embodiment, the method is utilized to treat low blood pressure. In an embodiment, the method is utilized to treat cancers. In an embodiment, the method is utilized to treat heart diseases. In an embodiment, the method is utilized to treat vegetative state. In an embodiment, the method is utilized to treat paralysis. In an embodiment, the method is utilized to reduce symptoms of varicose veins. In an embodiment, the method is utilized to treat kidney diseases. In an embodiment, the method is utilized to clean the blood vessels of plaques. In an embodiment, the method is utilized to treat a tropical disease. In an embodiment, the method is utilized to treat a disease caused by a virus. In an embodiment, the method is utilized to treat a condition caused by oxidative stress. In an embodiment, the method is utilized to treat or prevent stroke. In an embodiment, the method is utilized to prevent aging. In an embodiment, the method is improve human memory. In an embodiment, the method is utilized to treat erectile dysfunction. In an embodiment, the method is utilized to treat one of arthritis, joint pain, or combination thereof. In an embodiment, the method is utilized to control level of a cytokine.

In aspects, the method includes treating a disease comprising utilizing embodiments disclosed herein in coordination with an existing treatment method. In an embodiment, the existing treatment method is chemotherapy. In an embodiment, the existing treatment method is radiotherapy. In an embodiment, the existing treatment method is immunotherapy. In an embodiment, the existing treatment method is surgery. In an embodiment, the existing treatment method is dialysis.

In a further embodiment, a method is described. The method comprises mixing a therapeutic gas or a therapeutic liquid or a combination thereof and a liquid carrier in a high shear device to produce a therapeutic fluid, wherein said therapeutic fluid is a solution, a dispersion, or combination thereof and administering the produced therapeutic fluid intravenously to a patient; wherein the solution is supersaturated with the therapeutic gas, the therapeutic liquid, or combination thereof. In some cases, the solution is no less than 5% supersaturated.

In some embodiments, the therapeutic gas is selected from the group consisting of ozone, sulfur based gases, carbon monoxide, oxygen, hydrogen, nitrogen, an anesthetic gas, a noble gas, and mixtures thereof. In some embodiments, the therapeutic liquid is selected from the group consisting of sulfur, a sulfate, an organo metallic, an antibiotic, a steroid, a vitamin, an organosulfur compound, allyl propyl disulfide, diallyl disulfide (DADS or 4,5-dithia-1,7-octadiene), allyl trisulfide (DATS), S-Allyl cysteine (SAC), a vinyldithiine, a sulfonyl compound, an antioxidant, a lipid, a chelating agent, and combinations thereof.

In some embodiments, the antioxidant comprises curcumin (turmeric); wherein said chelating agent comprises diethylene triamine pentaacetic acid (DTPA); wherein said vinyldithiine comprises 2-vinyl-[4H]-1,3-dithiine or 3-vinyl-[4H]-1,2-dithiine; wherein said organosulfur compound comprises allicin; and wherein said sulfonyl compound comprises ajoene. In some embodiments, the therapeutic gas comprises hydrogen or hydrogen sulfide or oxygen.

In some embodiments, the therapeutic gas is oxygen and the produced therapeutic fluid is utilized in conjunction with a blood substitute. In some embodiments, a combination of therapeutic gases or a combination of therapeutic liquids or a combination of therapeutic gas and liquid is utilized.

In some embodiments, the liquid carrier comprises a total parenteral nutrition (TPN) solution. In some embodiments, the liquid carrier comprises an enhancer for carrying said therapeutic gas or said therapeutic liquid. In some embodiments, the method further comprises incorporating a medicine into the produced therapeutic fluid prior to administering the therapeutic fluid to the patient.

In some embodiments, the method as described above is utilized in conjunction with an existing treatment method to treat a disease.

In this disclosure, a method is described wherein the method comprises mixing a therapeutic gas or a therapeutic liquid or a combination thereof and a liquid carrier in a high shear device to produce a dispersion; and administering the produced dispersion intravenously to a patient; wherein the produced dispersion contains nanobubbles of the therapeutic gas or droplets of the therapeutic liquid with a mean diameter of less than about 1.5 µm.

In some embodiments, the therapeutic gas is selected from the group consisting of ozone, sulfur based gases, carbon monoxide, oxygen, hydrogen, nitrogen, an anesthetic gas, a noble gas, and mixtures thereof. In some embodiments, the therapeutic liquid is selected from the group consisting of sulfur, a sulfate, an organo metallic, an antibiotic, a steroid, a vitamin, an organosulfur compound, allyl propyl disulfide, diallyl disulfide (DADS or 4,5-dithia-1,7-octadiene), allyl trisulfide (DATS), S-Allyl cysteine (SAC), a vinyldithiine, a sulfonyl compound, an antioxidant, a lipid, a chelating agent, and combinations thereof. In some cases, the antioxidant comprises curcumin (turmeric); the chelating agent comprises diethylene triamine pentaacetic acid (DTPA); the vinyldithiine comprises 2-vinyl-[4H]-1,3-dithiine or 3-vinyl-[4H]-1,2-dithiine; the organosulfur compound comprises allicin; and the sulfonyl compound comprises ajoene.

In some embodiments, the method further comprises controlling the shear rate of the high shear device. In some embodiments, the method further comprises controlling the residence time of the therapeutic gas and liquid carrier in the high shear device. In some embodiments, the therapeutic gas is hydrogen and the produced dispersion reduces oxidative stress in the patient. In some embodiments, the therapeutic gas is hydrogen sulfide and the produced dispersion modulates vasoactivity of the patient. In some embodiments, the therapeutic gas is oxygen and the produced dispersion improves blood oxygenation of the patient. In some embodiments, the therapeutic gas is oxygen and the produced dispersion is utilized in conjunction with a blood substitute. In some embodiments, the produced dispersion is administered to a cancer patient and the therapeutic gas nanobubbles or dispersed nano sized immiscible therapeutic liquid contained therein destroy cancerous cells in the patient. In some embodiments, the produced dispersion is administered to a patient and the therapeutic gas nanobubbles or dispersed nano sized immiscible therapeutic liquid contained therein cause anesthetic effects in the patient.

In some embodiments, a combination of therapeutic gases is utilized. In some other embodiments, the liquid carrier comprises a total parenteral nutrition (TPN) solution. In yet other embodiments, the liquid carrier comprises an enhancer for carrying the therapeutic gas or liquid.

Without wishing to be limited by a theory, high shear enables the therapeutic gas and/or liquid to be carried in the liquid/lipid (TPN) to the desired location in the body without being degassed. It is possible that there is a bonding effect between the therapeutic gas/liquid and the fatty acid of the TPN, which is able to retain the gas/liquid more than the scenario when high shear is not utilized (e.g., the gas is only bubbled through a liquid/lipid for it to be dissolved).

In some embodiments the immiscible therapeutic liquid is a sulfur or organosulfur compound including allicin; diallyl disulfide (DADS or 4,5-dithia-1,7-octadiene); allyl propyl disulfide; diallyl trisulfide (DATS); S-Allyl cysteine (SAC); vinyldithiines (2-vinyl-[4H]-1,3-dithiine and 3-vinyl-[4H]-1,2-dithiine) and various sulfonyl compounds such as ajoene.

In some embodiments, the method further comprises incorporating a medicine into the produced dispersion prior to administering the dispersion to the patient. In some embodiments, the method disclosed herein is combined with an existing treatment method to treat a disease.

Also disclosed herein is a method comprising mixing a therapeutic agent, nanodiamonds, and a liquid carrier in a high shear device to produce a dispersion; and administering the produced dispersion intravenously to a patient.

In this disclosure, a system is described wherein the system comprises a therapeutic gas source or a therapeutic liquid source or a combination thereof; a liquid carrier source; a high shear device (HSD) having an inlet, an outlet, at least one rotor, and at least one stator separated by a shear gap, wherein the shear gap is the minimum distance between the at least one rotor and the at least one stator, and wherein the HSD inlet is in fluid communication with the therapeutic gas source or the therapeutic liquid source or both and the liquid carrier source; and a pump configured to control the flow rate and residence time of a fluid passing through the high shear device.

In some embodiments, the system further comprises a device configured for intravenous administration of fluid to a patient, said device having an inlet, wherein the inlet of the device is in fluid communication with the HSD outlet. In some embodiments, the system further comprises a storage vessel in fluid communication with the HSD. In some embodiments, the system further comprises a temperature control unit configured to control the temperature of the storage vessel. In some embodiments, the storage vessel is in fluid communication with the device configured for intravenous administration to the patient. In some embodiments, the system further comprises a temperature control unit configured to control the temperature of the HSD. In various embodiments, the passage of fluids is sterile. In some embodiments, the HSD is configured to produce a dispersion that contains nanobubbles of the therapeutic gas with a mean diameter of less than about 1.5 µm. In some embodiments, the HSD is capable of producing a tip speed of the at least one rotor of greater than 22.9 m/s (4,500 ft/min).

In some embodiments, the therapeutic gas source is configured to provide a gas selected from the group consisting of ozone, sulfur based gases, carbon monoxide, oxygen, hydrogen, nitrogen, an anesthetic gas, a noble gas, and combinations thereof. In some embodiments, the therapeutic liquid source is configured to provide a therapeutic liquid selected from the group consisting of sulfur, a sulfate, an organo metallic, an antibiotic, a steroid, a vitamin, an organosulfur compound, allyl propyl disulfide, diallyl disulfide (DADS or 4,5-dithia-1,7-octadiene), allyl trisulfide (DATS), S-Allyl cysteine (SAC), a vinyldithiine, a sulfonyl compound, an antioxidant, a lipid, a chelating agent, and combinations thereof.

The foregoing has outlined rather broadly the features and technical advantages of the invention in order that the detailed description of the invention that follows may be better understood. Additional features and advantages of the invention will be described hereinafter that form the subject of the claims of the invention. It should be appreciated by those skilled in the art that the conception and the specific embodiments disclosed may be readily utilized as a basis for modifying or designing other structures for carrying out the same purposes of the invention. It should also be realized by those skilled in the art that such equivalent constructions do not depart from the spirit and scope of the invention as set forth in the appended claims.

BRIEF DESCRIPTION OF THE DRAWINGS

For a more detailed description of the preferred embodiment of the present invention, reference will now be made to the accompanying drawings, wherein.

NOTATION AND NOMENCLATURE

Figure 1A:
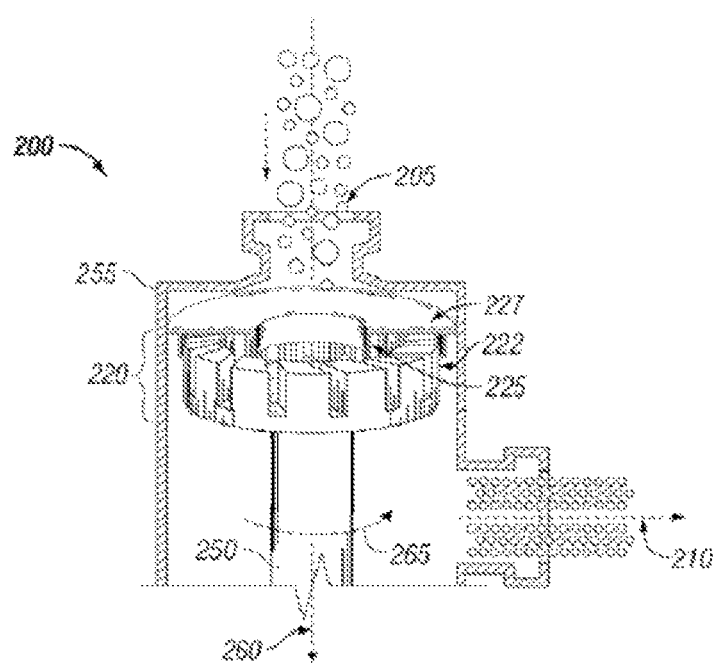
FIG. 1A is a longitudinal cross-section view of a one-stage shear device.

As used herein, the term "dispersion" refers to a liquefied mixture that contains at least two distinguishable substances (or "phases") that either will or will not readily mix and dissolve together. As used herein, a "dispersion" comprises a "continuous" phase (or "matrix"), which holds therein discontinuous droplets, bubbles, and/or particles of the other phase or substance. The term dispersion may thus refer to foams comprising gas bubbles suspended in a liquid continuous phase, emulsions in which droplets of a first liquid are dispersed throughout a continuous phase comprising a second liquid with which the first liquid is miscible or immiscible, and continuous liquid phases throughout which solid particles are distributed. As used herein, the term "dispersion" encompasses continuous liquid phases throughout which gas bubbles are distributed, continuous liquid phases throughout which solid particles are distributed, continuous phases of a first liquid throughout which droplets of a second liquid that is soluble or insoluble in the continuous phase are distributed, and liquid phases throughout which any one or a combination of solid particles, miscible/immiscible liquid droplets, and gas bubbles are distributed. Hence, a dispersion can exist as a homogeneous mixture in some cases (e.g., liquid/liquid phase), or as a heterogeneous mixture (e.g., gas/liquid, solid/liquid, or gas/solid/liquid), depending on the nature of the materials selected for combination.

As used herein, the term "therapeutic gas" refers to a gas or a combination of gases that have therapeutic effects for particular diseases. Some examples of therapeutic gases are ozone, sulfur based gases, carbon monoxide, oxygen, hydrogen. Other therapeutic gases would include inert gases, such as noble gases including argon, xenon. The therapeutic nature of these gases is derived from their ability to dissolve undesirable components within the body such as clots, cholesterol build-up and other compounds; their ability to apply pressure and thus mobility to restrictions in the circulatory system; and their ability to deliver therapeutic effects from oxidizing and/or reducing gases. Therapeutic effects of dissolved gases may also be derived from the use of toxic gases delivered to isolated portions of the body where tumors or other mutagenic cells exist. The delivery of the toxic therapeutic gas through the circulatory system to the isolated area destroys undesirable cells. Therapeutic gases may also include anesthetic gas or medicine that is in a gaseous state at room temperature that are dissolved and more safely and easily delivered as a dispersed fluid. The use of multiple gases either in combination or sequentially is also contemplated where multiple therapeutic methods are utilized. One such technique is to partially dissolve and then mobilize a clot or restriction by means of combinations of therapeutic gases. These therapeutic gases are utilized at a concentration/level that is efficacious and has minimal side effects.

As used herein immiscible therapeutic liquid refers to a liquid or combination of liquids that have therapeutic effects for particular diseases. Some examples of immiscible therapeutic liquids include various sulfate, organo metallic, antibiotics, steroids and certain vitamins. The immiscible nature refers to the ability to form a solution with blood plasma. In some instances the immiscible solution may be formed by combining or reacting a solid with a liquid such as the formation of organo metallic compounds by combining a metal with an organic compound. For ease of reference, a therapeutic gas is sometimes mentioned in this disclosure to refer to a therapeutic gas or a therapeutic liquid or a combination thereof. It is within the scope of this disclosure that a therapeutic gas or a therapeutic liquid or a combination thereof may be utilized where a therapeutic gas is explicitly recited.

As used herein, the term "disease" refers to an abnormal condition affecting the body of a human.

Certain terms are used throughout the following description and claims to refer to particular system components. This document does not intend to distinguish between components that differ in name but not function.

In the following description and in the claims, the terms "including" and "comprising" are used in an open-ended fashion, and thus should be interpreted to mean "including, but not limited to . . . ".

DETAILED DESCRIPTION

Shear Device

Shear device is a mechanical device that utilizes one or more generator comprising a rotor/stator combination, each of which has a gap between the stator and rotor. The gap between the rotor and the stator in each generator set may be fixed or may be adjustable. Shear device is configured in such a way that it is capable of producing submicron and micron-sized bubbles or nano-size particles in a mixture flowing through the high shear device. The high shear device comprises an enclosure or housing so that the pressure and temperature of the mixture may be controlled.

High shear mixing devices are generally divided into three general classes, based upon their ability of mixing/dispersing. Mixing is the process of reducing the size of particles or inhomogeneous species within the fluid. One metric for the degree or thoroughness of mixing is the energy density per unit volume that the mixing device generates to disrupt the fluid particles. The classes are distinguished based on delivered energy densities. Three classes of industrial mixers having sufficient energy density to consistently produce mixtures or emulsions with particle sizes in the range of submicron to 50 microns include homogenization valve systems, colloid mills and high speed mixers. In the first class of high energy devices, referred to as homogenization valve systems, fluid to be processed is pumped under very high pressure through a narrow-gap valve into a lower pressure environment. The pressure gradients across the valve and the resulting turbulence and cavitation act to break-up any particles in the fluid. These valve systems are most commonly used in milk homogenization and can yield average particle sizes in the submicron to about 1 micron range.

At the opposite end of the energy density spectrum is the third class of devices referred to as low energy devices. These systems usually have paddles or fluid rotors that turn at high speed in a reservoir of fluid to be processed, which in many of the more common applications is a food product. These low energy systems are customarily used when average particle sizes of greater than 20 microns are acceptable in the processed fluid.

Between the low energy devices and homogenization valve systems, in terms of the mixing energy density delivered to the fluid, are colloid mills and other high speed rotor-stator devices, which are classified as intermediate energy devices. A typical colloid mill configuration includes a conical or disk rotor that is separated from a complementary, liquid-cooled stator by a closely-controlled rotor-stator gap, which is commonly between 0.0254 mm to 10.16 mm (0.001-0.40 inch). Rotors are usually driven by an electric motor through a direct drive or belt mechanism. As the rotor rotates at high rates, it pumps fluid between the outer surface of the rotor and the inner surface of the stator, and shear forces generated in the gap process the fluid. Many colloid mills with proper adjustment achieve average particle sizes of 0.1-25 microns in the processed fluid. These capabilities render colloid mills appropriate for a variety of applications including colloid and oil/water-based emulsion processing such as that required for cosmetics, mayonnaise, or silicone/silver amalgam formation, to roofing-tar mixing.

Tip speed is the circumferential distance traveled by the tip of the rotor per unit of time. Tip speed is thus a function of the rotor diameter and the rotational frequency. Tip speed (in meters per minute, for example) may be calculated by multiplying the circumferential distance transcribed by the rotor tip, $2\pi R$, where R is the radius of the rotor (meters, for example) times the frequency of revolution (for example revolutions per minute, rpm). A colloid mill, for example, may have a tip speed in excess of 22.9 m/s (4500 ft/min) and may exceed 40 m/s (7900 ft/min). For the purpose of this disclosure, the term 'high shear' refers to mechanical rotor stator devices (e.g., colloid mills or rotor-stator dispersers) that are capable of tip speeds in excess of 5.1 m/s. (1000 ft/min) and require an external mechanically driven power device to drive energy into the feed stream to be processed. For example, in a shear device, a tip speed in excess of 22.9 m/s (4500 ft/min) is achievable, and may exceed 40 m/s (7900 ft/min). In some embodiments, a shear device is capable of delivering at least 300 L/h at a tip speed of at least 22.9 m/s (4500 ft/min). The power consumption will vary depending on the viscosity, temperature and pressure of operation. Shear device combines high tip speed with a very small shear gap to produce significant shear on the material being processed. The amount of shear will be dependent on the viscosity of the fluid. Accordingly, a local region of elevated pressure and temperature is created at the tip of the rotor during operation of the high shear device. In some cases the locally elevated pressure is about 1034.2 MPa (150,000 psi). In some cases the locally elevated temperature is about 500° C. In some cases, these local pressure and temperature elevations may persist for nano or pico seconds.

Without wishing to be limited to a particular theory, it is believed that the level or degree of high shear mixing is sufficient to produce localized non-ideal conditions. Localized non-ideal conditions are believed to occur within the high shear device resulting in increased temperatures and pressures with the most significant increase believed to be in localized pressures. The increase in pressures and temperatures within the high shear device are instantaneous and localized and quickly revert back to bulk or average system conditions once exiting the high shear device. In some cases, the high shear mixing device induces cavitation of sufficient intensity to dissociate one or more of the feed stream components into free radicals, which may intensify an interaction (e.g., a chemical reaction) or allow an interaction to take place at less stringent conditions than might otherwise be required. Cavitation may also increase rates of transport processes by producing local turbulence and liquid micro-circulation (acoustic streaming). An overview of the application of cavitation phenomenon in chemical/physical processing applications is provided by Gogate et al., "Cavitation: A technology on the horizon," *Current Science* 91 (No. 1): 35-46 (2006).

An approximation of energy input into the fluid (kW/L/min) can be estimated by measuring the motor energy (kW) and fluid output (L/min). As mentioned above, tip speed is the velocity (ft/min or m/s) associated with the end of the one or more revolving elements that is creating the mechanical force applied to the feed stream components. In embodiments, the energy expenditure of shear device is greater than 1000 W/m$^3$. In embodiments, the energy expenditure of shear device is in the range of from about 3000 W/m$^3$ to about 7500 W/m$^3$.

The shear rate is the tip speed divided by the shear gap width (minimal clearance between the rotor and stator). The shear rate generated in a shear device may be in the greater than 20,000 s$^{-1}$. In some embodiments the shear rate is at least 40,000 s$^{-1}$. In some embodiments the shear rate is at least 100,000 s$^{-1}$. In some embodiments the shear rate is at least 500,000 s$^{-1}$. In some embodiments the shear rate is at least 1,000,000 s$^{-1}$. In some embodiments the shear rate is at least 1,600,000 s$^{-1}$. In embodiments, the shear rate generated by a shear device is in the range of from 20,000 s$^{-1}$ to 100,000 s$^{-1}$. For example, in one application the rotor tip speed is about 40 m/s (7900 ft/min) and the shear gap width is 0.0254 mm (0.001 inch), producing a shear rate of 1,600,000 s$^{-1}$. In another application the rotor tip speed is about 22.9 m/s (4500 ft/min) and the shear gap width is 0.0254 mm (0.001 inch), producing a shear rate of about 901,600 s$^{-1}$. In some embodiments, shear device comprises a colloid mill. Suitable colloidal mills are manufactured by IKA® Works, Inc. Wilmington, N.C. and APV North America, Inc. Wilmington, Mass., for example. In some instances, shear device comprises the DISPAX REACTOR® of IKA® Works, Inc.

The high shear device comprises at least one revolving element that creates the mechanical force applied to the stream that passes through. The high shear device comprises at least one stator and at least one rotor separated by a clearance. For example, the rotors may be conical or disk shaped and may be separated from a complementarily-shaped stator. In embodiments, both the rotor and stator comprise a plurality of circumferentially-spaced teeth. In some embodiments, the stator(s) are adjustable to obtain the desired shear gap between the rotor and the stator of each generator (rotor/stator set). Grooves between the teeth of the rotor and/or stator may alternate direction in alternate stages for increased turbulence. Each generator may be driven by any suitable drive system configured for providing the necessary rotation.

In some embodiments, the minimum clearance (shear gap width) between the stator and the rotor is in the range of from about 0.0254 mm (0.001 inch) to about 3.175 mm (0.125 inch). In certain embodiments, the minimum clearance (shear gap width) between the stator and rotor is about 1.52 mm (0.060 inch). In certain configurations, the minimum clearance (shear gap) between the rotor and stator is at least 1.78 mm (0.07 inch). The shear rate produced by the high shear device may vary with longitudinal position along the flow pathway. In some embodiments, the rotor is set to rotate at a speed commensurate with the diameter of the rotor and the desired tip speed. In some embodiments, the high shear device has a fixed clearance (shear gap width) between the stator and rotor. Alternatively, the high shear device has adjustable clearance (shear gap width).

In some embodiments, a shear device comprises a single stage dispersing chamber (i.e., a single rotor/stator combination, a single generator). In some embodiments, a shear device is a multiple stage inline disperser and comprises a plurality of generators. In certain embodiments, a shear device comprises at least two generators. In other embodiments, a shear device comprises at least 3 high shear generators. In some embodiments, a shear device is a multistage mixer whereby the shear rate (which, as mentioned above, varies proportionately with tip speed and inversely with rotor/stator gap width) varies with longitudinal position along the flow pathway, as further described herein below.

In some embodiments, each stage of the shear device has interchangeable mixing tools, offering flexibility. For example, the DR 2000/4 DISPAX REACTOR® of IKA® Works, Inc. Wilmington, N.C. and APV North America, Inc. Wilmington, Mass., comprises a three stage dispersing module. This module may comprise up to three rotor/stator combinations (generators), with choice of fine, medium, coarse, and super-fine for each stage. This allows for creation of dispersions having a narrow distribution of the desired bubble size and particle size. In some embodiments, each of the stages is operated with super-fine generator. In some embodiments, at least one of the generator sets has a rotor/stator minimum clearance (shear gap width) of greater than about 5.0 mm (0.20 inch). In alternative embodiments, at least one of the generator sets has a minimum rotor/stator clearance of greater than about 1.78 mm (0.07 inch).

FIG. 1A presents a longitudinal cross-section of a suitable shear device 200. Shear device 200 of FIG. 1A is a dispersing device comprising a combination 220 of a rotor 222 and a stator 227. The rotor-stator combination may be known as generator 220 or stage without limitation. The rotor 222 and stator 227 are fitted along drive shaft 250.

For generator 220, the rotor 222 is rotatably driven by input 250 and rotates about axis 260 as indicated by arrow 265. The direction of rotation may be opposite that shown by arrow 265 (e.g., clockwise or counterclockwise about axis of rotation 260). Stator 227 is fixably coupled to the wall 255 of shear device 200. Generator 220 has a shear gap width which is the minimum distance between the rotor and the stator. In the embodiment of FIG. 1A, generator 220 comprises a shear gap 225.

Generator 220 may comprise a coarse, medium, fine, and super-fine characterization. Rotors 222 and stators 227 may be toothed designs. Generator 220 may comprise two or more sets of rotor-stator teeth. In embodiments, rotor 222 comprises rotor teeth circumferentially spaced about the circumference of the rotor. In embodiments, stator 227 comprises stator teeth circumferentially spaced about the circumference of the stator.

Shear device 200 is configured for receiving fluid mixtures at inlet 205. Fluid mixtures entering inlet 205 are pumped serially through generator 220, such that product dispersions are formed. Product dispersions exit shear device 200 via outlet 210. Rotor 222 of generator 220 rotates at a speed relative to the fixed stator 227, providing adjustable shear rates. The rotation of the rotor pumps fluid, such as the fluid mixtures entering inlet 205, outwardly through the shear gaps (and, if present, through the spaces between the rotor teeth and the spaces between the stator teeth), creating a localized shear condition. Shear forces exerted on fluid in shear gap 225 (and, when present, in the gaps between the rotor teeth and the stator teeth) through which fluid flows process the fluid and create product dispersion. Product dispersion exits shear device 200 via shear outlet 210.

In certain instances, shear device 200 comprises a ULTRA-TURRAX® of IKA® Works, Inc. Wilmington, N.C. Several models are available having variable sizes, volume capacities, flow rates, tip speeds, inlet/outlet connections, horsepower, output rpm, and operable temperature ranges. For example, the T 10 basic ULTRA-TURRAX® homogenizer provides a stepless control of speed with a speed range of 8000-30000 min⁻¹ and adjustable dispersing elements.

In certain embodiments, more than one stage or combination of rotor and stator may be employed. For example, two or three stages of rotor-stator combinations are connected serially along the same drive shaft to enable flexibility to provide variable shear stress. Fluid mixtures are passed through different stages of rotor-stator combinations to be processed serially until the desired dispersion products are formed. Examples of adjustable operational parameters are rotor size, stator size, shear gap, rotor speed, tip speed, shear rate, flow rate, residence time.

Figure 1B:
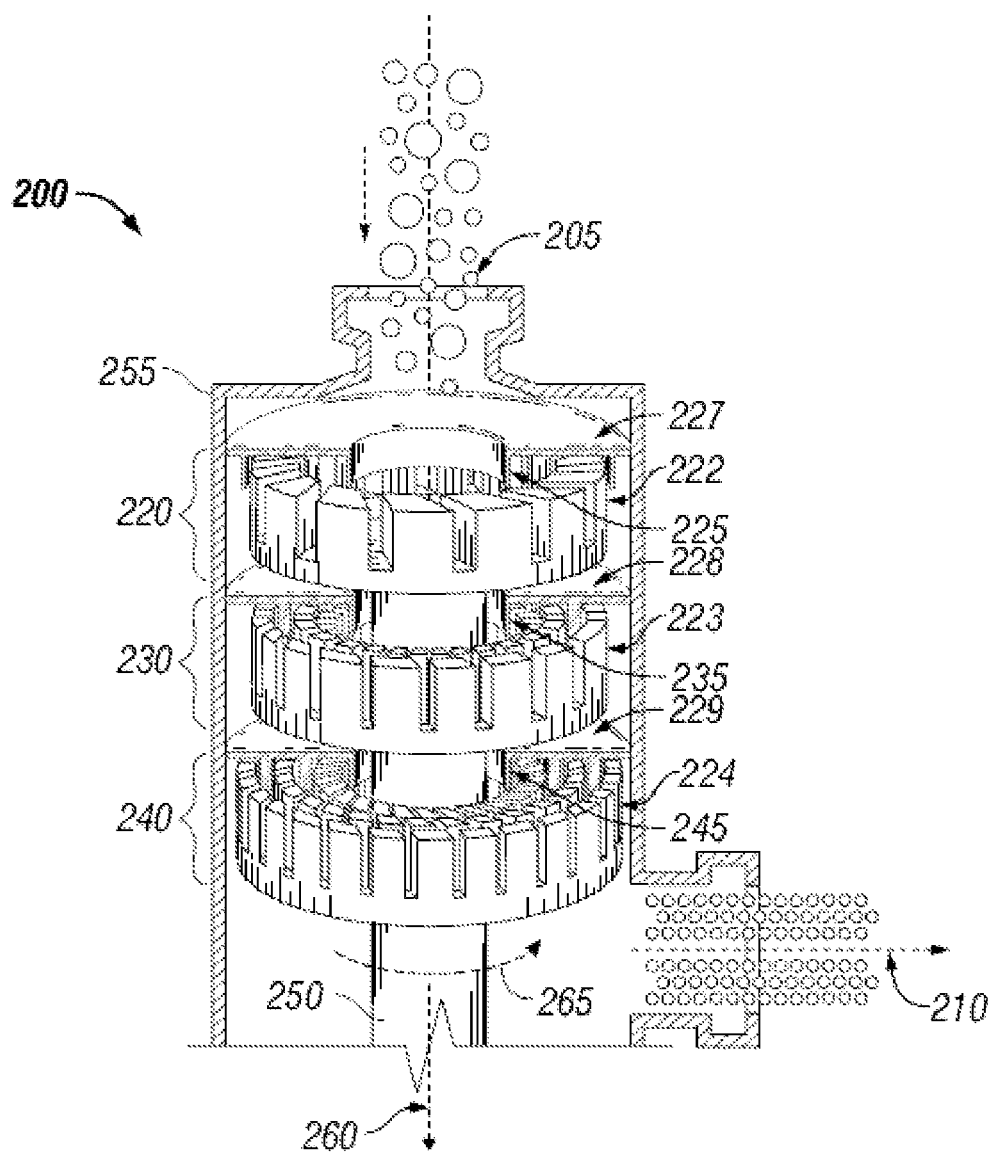
FIG. 1B is a longitudinal cross-section view of a three-stage shear device.

FIG. 1B presents a longitudinal cross-section of a three-stage shear device 200, comprising three stages or rotor-stator combinations 220, 230, and 240 as a dispersing device. The rotor-stator combinations may be known as generators 220, 230, 240 or stages without limitation. Three rotor/stator sets or generators 220, 230, and 240 are aligned in series along drive shaft 250.

First generator 220 comprises rotor 222 and stator 227. Second generator 230 comprises rotor 223, and stator 228. Third generator 240 comprises rotor 224 and stator 229. For each generator the rotor is rotatably driven by input 250 and rotates about axis 260 as indicated by arrow 265. The direction of rotation may be opposite that shown by arrow 265 (e.g., clockwise or counterclockwise about axis of rotation 260). Stators 227, 228, and 229 are fixably coupled to the wall 255 of high shear device 200.

As mentioned hereinabove, each generator has a shear gap width which is the minimum distance between the rotor and the stator. In the embodiment of FIG. 1B, first generator 220 comprises a first shear gap 225; second generator 230 comprises a second shear gap 235; and third generator 240 comprises a third shear gap 245. In embodiments, shear gaps 225, 235, 245 have widths in the range of from about 0.025 mm to about 10.0 mm. Alternatively, the process comprises utilization of a high shear device 200 wherein the gaps 225, 235, 245 have a width in the range of from about 0.5 mm to about 2.5 mm. In certain instances the shear gap width is maintained at about 1.5 mm. Alternatively, the width of shear gaps 225, 235, 245 are different for generators 220, 230, 240. In certain instances, the width of shear gap 225 of first generator 220 is greater than the width of shear gap 235 of second generator 230, which is in turn greater than the width of shear gap 245 of third generator 240. As mentioned above, the generators of each stage may be interchangeable, offering flexibility. High shear device 200 may be configured so that the shear rate will increase stepwise longitudinally along the direction of the flow 260.

Generators 220, 230, and 240 may comprise a coarse, medium, fine, and super-fine characterization. Rotors 222, 223, and 224 and stators 227, 228, and 229 may be toothed designs. Each generator may comprise two or more sets of rotor-stator teeth. In embodiments, rotors 222, 223, and 224 comprise more than 10 rotor teeth circumferentially spaced about the circumference of each rotor. In embodiments, stators 227, 228, and 229 comprise more than ten stator teeth circumferentially spaced about the circumference of each stator. In embodiments, the inner diameter of the rotor is about 12 cm. In embodiments, the diameter of the rotor is about 6 cm. In embodiments, the outer diameter of the stator is about 15 cm. In embodiments, the diameter of the stator is about 6.4 cm. In some embodiments the rotors are 60 mm and the stators are 64 mm in diameter, providing a clearance of about 4 mm. In certain embodiments, each of three stages is operated with a super-fine generator, comprising a shear gap of between about 0.025 mm and about 4 mm. For applications in which solid particles are to be sent through high shear device 40, the appropriate shear gap width (minimum clearance between rotor and stator) may be selected for an appropriate reduction in particle size and increase in particle surface area. In embodiments, this may be beneficial for increasing surface area of solid drugs by shearing and dispersing the particles.

High shear device 200 is configured for receiving a feed stream at inlet 205. Feed stream entering inlet 205 is pumped serially through generators 220, 230, and then 240, such that a dispersion is formed. The dispersion exits high shear device 200 via outlet 210. The rotors 222, 223, 224 of each generator rotate at high speed relative to the fixed stators 227, 228, 229, providing a high shear rate. The rotation of the rotors pumps fluid, such as the feed stream entering inlet 205, outwardly through the shear gaps (and, if present, through the spaces between the rotor teeth and the spaces between the stator teeth), creating a localized high shear condition. High shear forces exerted on fluid in shear gaps 225, 235, and 245 (and, when present, in the gaps between the rotor teeth and the stator teeth) through which fluid flows process the fluid and create the dispersion. The product dispersion exits high shear device 200 via high shear outlet 210.

The produced dispersion has an average gas bubble size less than about 5 µm. In embodiments, shear device 200 produces a dispersion having a mean bubble size of less than about 1.5 µm. In embodiments, shear device 200 produces a dispersion having a mean bubble size of less than 1 µm; preferably the bubbles are sub-micron in diameter. In certain instances, the average bubble size is from about 0.1 µm to about 1.0 µm. In embodiments, shear device 200 produces a dispersion having a mean bubble size of less than 400 nm. In embodiments, shear device 200 produces a dispersion having a mean bubble size of less than 100 nm. Shear device 200 produces a dispersion comprising dispersed gas bubbles capable of remaining dispersed at atmospheric pressure for at least about 15 minutes.

In certain instances, high shear device 200 comprises a DISPAX REACTOR® of IKA® Works, Inc. Wilmington, N.C. and APV North America, Inc. Wilmington, Mass. Several models are available having various inlet/outlet connections, horsepower, tip speeds, output rpm, and flow rate. Selection of the high shear device will depend on throughput requirements and desired particle or bubble size in dispersion exiting outlet 210 of high shear device 200. IKA® model DR 2000/4, for example, comprises a belt drive, 4M generator, PTFE sealing ring, inlet flange 25.4 mm (1 inch) sanitary clamp, outlet flange 19 mm (¾ inch) sanitary clamp, 2HP power, output speed of 7900 rpm, flow capacity (water) approximately 300-700 L/h (depending on generator), a tip speed of from 9.4-41 m/s (1850 ft/min to 8070 ft/min).

Application of Shear in Medical Therapy
Application of Shear in Medical Therapy

Figure 2A:
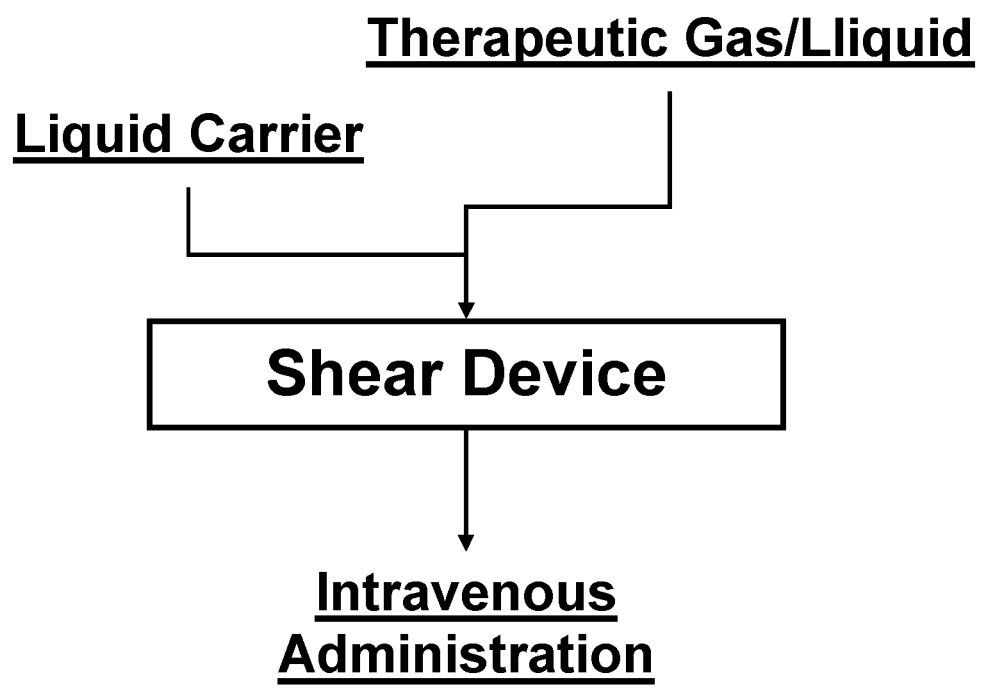
FIG. 2A illustrates a method of utilizing a shear device for medical therapy.

In an embodiment as illustrated by FIG. 2A, the application of shear comprises passing a therapeutic gas or immiscible therapeutic liquid or a combination thereof and a liquid carrier through a shear device as described herein to produce a dispersion, wherein the dispersion contains nanobubbles of said gas or nanoparticles/nanoglobules of said therapeutic liquid. As used herein, "nanobubbles" or "nanoparticles" or "nanoglobules" refers to gas bubbles or liquid droplets with a size in the range of from sub-nanometers to 1000 nanometers in diameter. In some embodiments, the shear device produces a dispersion having a mean bubble or droplet size of less than about 5 µm in diameter. In some embodiments, the bubbles or droplets in the produced dispersion are sub-micron in diameter. In some embodiments, the average bubble or droplet size is from about 0.1 µm to about 5 µm in diameter. In some embodiments, the shear device produces a dispersion having a mean bubble or droplet size of less than 400 nm in diameter. In some embodiments, the shear device produces a dispersion having a mean bubble or droplet size of less than 100 nm in diameter. In an embodiment, the application of shear further comprises administering the dispersion containing the gas nanobubbles or dispersed nano sized immiscible therapeutic liquid to a patient intravenously (e.g., intravenous infusion, intravenous injection). The liquid carrier may be any suitable liquid known to one skilled in the art, e.g., saline solution, lactated Ringer's solution, acetated Ringer's solution.

In some embodiments, the liquid carrier comprises total parenteral nutrition (TPN). TPN is able to supply to a patient all daily nutritional requirements. In some cases, it is used in the hospital. In other cases, it is used at home. Since TPN solutions are concentrated and may cause thrombosis of peripheral veins, a central venous catheter is used for administration in such embodiments. The use of TPN depends on the condition of patients, for example, TPN may be the only feasible option for patients who do not have a functioning GI tract or who have disorders requiring complete bowel rest, such as some stages of Crohn's disease or ulcerative colitis, bowel obstruction, certain pediatric GI disorders (e.g., congenital GI anomalies, prolonged diarrhea regardless of its cause), short bowel syndrome due to surgery. The preparation and administration of the liquid carrier comprising TPN is carried out using sterile techniques. Other type of liquid emulsions may also be incorporated into the liquid carrier.

The therapeutic gas or immiscible therapeutic liquid is subjected to a suitable shear rate for a period of time so that the produced dispersion exiting the shear device contains nanobubbles of the gas or nano-droplets of the therapeutic liquid.

The shear rate generated in high shear device (HSD) may be greater than 20,000 s$^{-1}$. In some embodiments the shear rate is at least 40,000 s$^{-1}$. In some embodiments the shear rate is at least 100,000 s$^{-1}$. In some embodiments the shear rate is at least 500,000 s$^{-1}$. In some embodiments the shear rate is at least 1,000,000 s$^{-1}$. In some embodiments the shear rate is at least 1,600,000 s$^{-1}$. In embodiments, the shear rate generated by HSD is in the range of from 20,000 s$^{-1}$ to 100,000 s$^{-1}$. For example, in one application the rotor tip speed is about 40 m/s (7900 ft/min) and the shear gap width is 0.0254 mm (0.001 inch), producing a shear rate of 1,600,000 s$^{-1}$. In another application the rotor tip speed is about 22.9 m/s (4500 ft/min) and the shear gap width is 0.0254 mm (0.001 inch), producing a shear rate of about 901,600 s$^{-1}$. In some embodiments, the produced dispersion (or therapeutic fluid) is immediately administered to a patient intravenously. The dispersion may be stable for at least about 15 minutes at atmospheric pressure.

Selection of the shear device, shear rate, shear stress, and residence time applied in shear device depends on the amount of therapeutic fluid needed, the concentration of gas or therapeutic liquid contained therein, and the size of the gas nanobubbles or dispersed nano sized immiscible therapeutic liquid desired. For example, higher gas concentrations and smaller gas bubbles may require longer residence times.

Figure 2B:
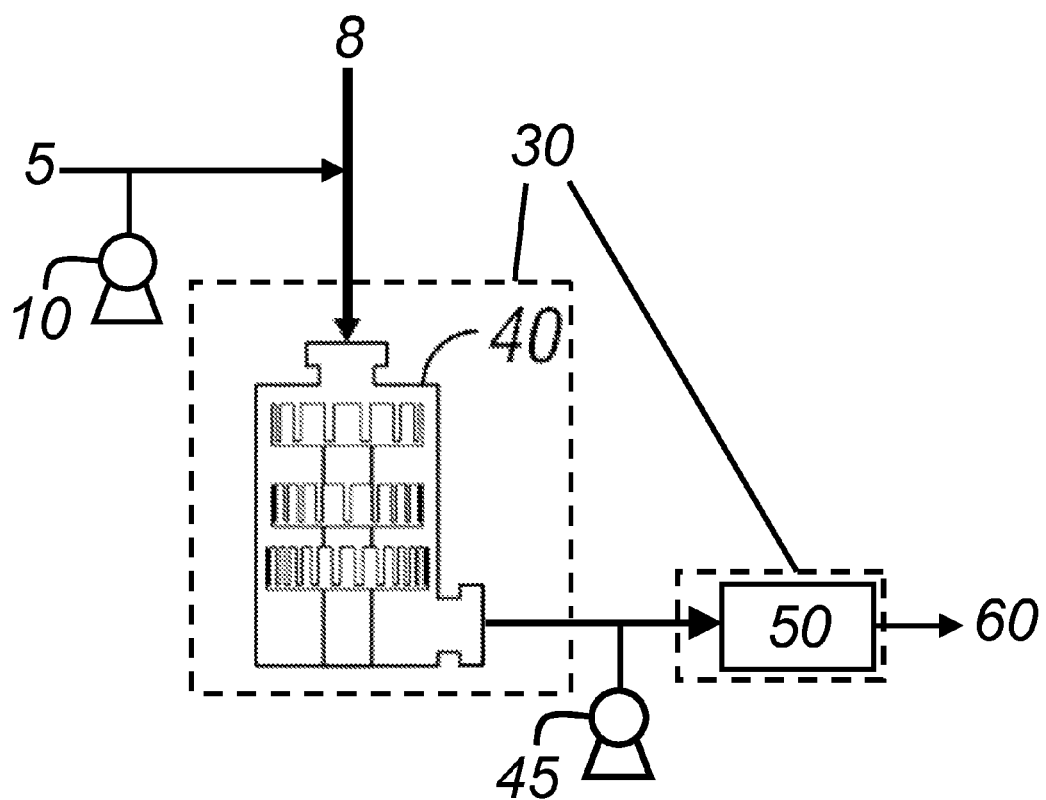
FIG. 2B is a process flow diagram demonstrating the application of shear stress for medical therapy.

Referring to FIG. 2B, a liquid carrier 5 and a therapeutic gas or immiscible therapeutic liquid or a combination thereof 8 are introduced into shear device 40 (at inlet 205 in FIGS. 1A and 1B). The therapeutic gas or immiscible therapeutic liquid is dispersed into nanobubbles or nano-droplets in the liquid carrier. In some embodiments, a pump 10 is included to control the flow rate of the liquid carrier into shear device 40. Pump 10 is configured for either continuous or semi-continuous operation, and may be any suitable pumping device. In some embodiments, a pump is used to control the flow rate of the therapeutic gas into shear device 40 (not shown in FIG. 2B).

In some embodiments, the temperature of shear device 40 is maintained by a temperature control unit 30, wherein said temperature control unit 30 is any device known to one skilled in the art and has the capacity to maintain a temperature between 0-100° C. within ±2° C. fluctuations. Shear device 40 is configured to be in fluid connection (at outlet 210 in FIGS. 1A and 1B) with vessel 50, wherein said fluid connection may be any as known to one skilled in the art. The temperature of vessel 50 is maintained by a temperature control unit 30, wherein said temperature control unit 30 is any device known to one skilled in the art and has the capacity to maintain a temperature between 0-100° C. within ±2° C. fluctuations. In some embodiments, a pump 45 is included to control the flow rate of the produced dispersion (i.e., therapeutic fluid) entering vessel 50. Pump 45 is configured for either continuous or semi-continuous operation, and may be any suitable pumping device. In some cases, the produced dispersion or therapeutic fluid 60 containing gas nanobubbles or dispersed nano sized immiscible therapeutic liquid is administered to a patient intravenously.

In some embodiments, the application of shear is especially useful in creating therapeutic fluids. For example, ozone as a therapeutic gas is dispersed in saline solution into gas bubbles that are on the nano or sub-nano scale. When such dispersions are injected or infused into patients, ozone gas is circulated in the bloodstream and transported to various organs and tissues. Because the size of the produced gas bubbles are small (nano-, sub-nano-size), ozone gas has the potential to overcome the blood brain barrier (BBB) to obtain access to the brain and therefore become effective therapeutically.

Figure 3:
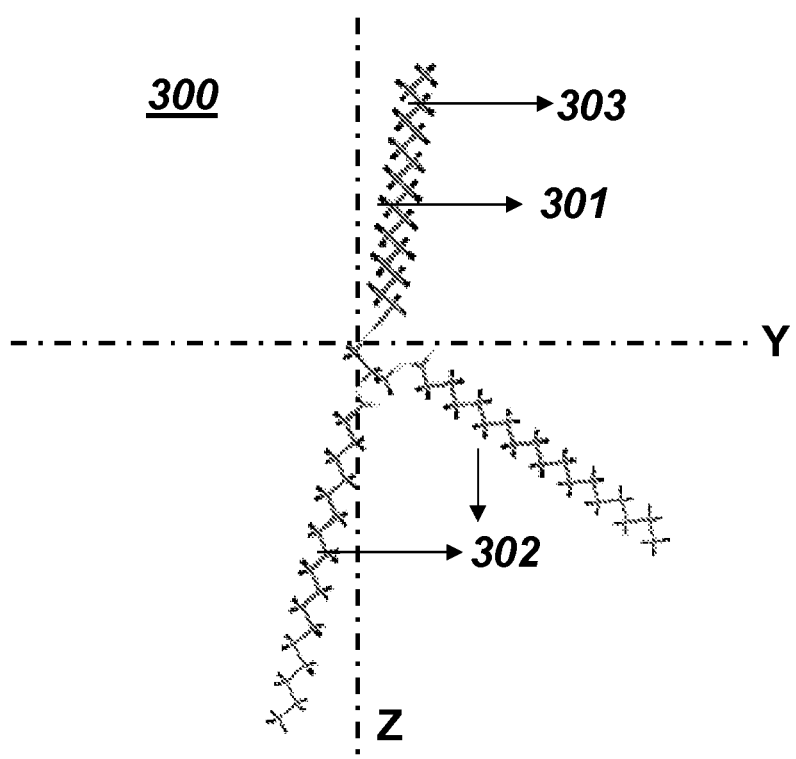
FIG. 3 illustrates an enhancer molecule for carrying a gas in a liquid medium.

In some embodiments, the liquid carrier comprises an enhancer for carrying the therapeutic gas or immiscible therapeutic liquid. For example, molecule 300 as shown in FIG. 3 may be used. Molecule 300 is tristearin (or 1,3-Di(octadecanoyloxy)propan-2-yl octadecanoate or tristearin or trioctadecanoin or glycerol tristearate or glyceryl tristearate), which is a triglyceride, a glyceryl ester of stearic acid, derived from fats. Molecule 300 has backbone 301, branches 302, and vacant ports 303. Furthermore, molecule 300 is able to freely spin around axis Y or axis Z. Gas molecules are latched unto such an enhancer (molecule 300) via the vacant ports 303, especially under the action of high shear. The use of such an enhancer promotes the transport of the therapeutic gas or immiscible therapeutic liquid to the target site and thus increases the efficacy of the treatment.

By producing counterpart free radicals under high shear action, the method disclosed herein is able to reverse the damaging effects caused by free radicals. The term "counterpart free radicals" as used herein refers to free radicals that cause neutralizing or remedial effects of damaging free radicals. For example, oxygen may be a damaging free radical in some processes and in this case hydrogen is the counterpart free radical, which is able to reverse the damaging effects caused by the oxygen radical (e.g., oxidative stress, gene mutation, cancer). In other instances the free radical creates an ionic charge on the therapeutic gas or liquid compound. The charged therapeutic compound is then preferentially attracted to the surface of certain tumor cells resulting in more targeted treatment of malignant cells.

Super-saturation. In some embodiments, the application of high shear enables the liquid carrier to be super-saturated with the therapeutic gas, the therapeutic liquid, or a combination thereof (compared to when high shear is not applied) and produces a stable solution. In this disclosure, super saturation means that the solution (or the solvent) contains an amount of solute more than the amount of solute at equilibrium state when compared at the same condition. The percentage of the excess amount of solute is a measure of the degree of super saturation of the solution.

In some embodiments, the super-saturated solution is stable at ambient conditions for extended periods of time. In some embodiments, the release of the therapeutic gas from the solution requires the application of vacuum. In various embodiments, the produced solution is utilized to treat a disease as described herein.

In some cases, the solution is no less than 5% supersaturated with the therapeutic gas, the therapeutic liquid, or a combination thereof. In some cases, the solution is no less than 10% supersaturated with the therapeutic gas, the therapeutic liquid, or a combination thereof. In some cases, the solution is no less than 15% supersaturated with the therapeutic gas, the therapeutic liquid, or a combination thereof. In some cases, the solution is no less than 20% supersaturated with the therapeutic gas, the therapeutic liquid, or a combination thereof. In some cases, the solution is no less than 25% supersaturated with the therapeutic gas, the therapeutic liquid, or a combination thereof. In some cases, the solution is no less than 30% supersaturated with the therapeutic gas, the therapeutic liquid, or a combination thereof. In some cases, the solution is no less than 35% supersaturated with the therapeutic gas, the therapeutic liquid, or a combination thereof. In some cases, the solution is no less than 40% supersaturated with the therapeutic gas, the therapeutic liquid, or a combination thereof. In some cases, the solution is no less than 45% supersaturated with the therapeutic gas, the therapeutic liquid, or a combination thereof. In some cases, the solution is no less than 50% supersaturated with the therapeutic gas, the therapeutic liquid, or a combination thereof.

EXAMPLES

The therapeutic gas/liquid is mixed with a liquid carrier in a high shear device as described herein to produce a therapeutic fluid, wherein the therapeutic fluid is a dispersion, a solution, or combination thereof. For ease of reference, such a therapeutic fluid may also be referred to as dispersion/solution in the examples provided below.

Oxidative Stress Reduction.

In an embodiment, hydrogen ($H_2$) as a therapeutic gas is processed in a shear device as described herein to reduce the level of oxidative stress in a patient. Without wishing to be limited by a theory, when the produced dispersion/solution (or therapeutic fluid) is introduced into a patient, the hydrogen nanobubbles contained therein reduce the amount of ROS and restore the necessary redox balance in the patient. Thus, cell damage due to oxidative stress is reduced and the various conditions (e.g., aging, stroke) associated with oxidative stress are alleviated. Levels of therapeutic gases in the dispersion/solution depend upon injection rate into the body and also the threshold level beyond which the gas concentration may no longer be therapeutic and may become toxic. The gas concentration is thereby determined by the level at which the desired therapeutic effect is observed.

Blood Oxygenation.

In an embodiment, oxygen ($O_2$) as a therapeutic gas is processed in a shear device as described herein to facilitate blood oxygenation in a patient. Without wishing to be limited by a theory, when the produced dispersion/solution (or therapeutic fluid) is introduced into a patient, the oxygen nanobubbles contained therein improve the level of blood oxygenation in the patient. Levels of therapeutic gases in the dispersion/solution depend upon injection rate into the body and also the threshold level beyond which the gas concentration may no longer be therapeutic and may become toxic. The gas concentration is thereby determined by the level at which the desired therapeutic effect is observed. In some cases, the produced dispersion/solution is used in conjunction with blood substitutes, hemoglobin-based oxygen carriers (HBOCs) or perfluorocarbon emulsions (PFCs).

Modulation of Vasoactivity.

In an embodiment, hydrogen sulfide ($H_2S$) as a therapeutic gas is processed in a shear device as described herein to modulate vasoactivity of a patient. It has been found that hydrogen sulfide ($H_2S$) is an endogenous cardioprotective vascular cell signaling molecule (see, for example, Benavides et. al., Proceedings of the National Academy of Sciences, Vol. 104, No. 46, 17977-17982). In vivo and in vitro cardiovascular effects of $H_2S$ include decreased blood pressure, cardioprotection against ischemic reperfusion damage, and $O_2$-dependent vasorelaxation. Without wishing to be limited by a theory, when the produced dispersion/solution (or therapeutic fluid) is introduced into a patient, the hydrogen sulfide nanobubbles contained therein facilitate the modulation of vasoactivity in the patient. In some cases, the hydrogen sulfide nanobubbles introduced into the patient reduce multiple risk factors associated with cardiovascular diseases, such as increased reactive oxygen species, high blood pressure, high cholesterol, platelet aggregation, and blood coagulation. Levels of therapeutic gases in the dispersion/solution (or in the liquid carrier) depend upon injection rate into the body and also the threshold level beyond which the gas concentration may no longer be therapeutic and may become toxic. For gases such as hydrogen sulfide, a toxic level in the body is believed to average around 300-350 ppm. The gas concentration is thereby determined by the level at which the therapeutic effect is observed with minimal side effects.

Cancer Treatment.

In an embodiment, a therapeutic gas or immiscible therapeutic liquid is processed in a shear device as described herein to treat cancer in a patient. Without wishing to be limited by a theory, when the produced dispersion/solution (or therapeutic fluid) is introduced into a patient, the gas nanobubbles or dispersed nano sized immiscible therapeutic liquid contained therein are able to destroy cancerous cells while sparing healthy/normal cells in the patient because the cancerous cells are weaker compared to the normal cells. Such treatment is especially useful in treating hematological malignancies, such as leukemia, lymphoma, and multiple myeloma. Suitable therapeutic gases include ozone, sulfur based gases, carbon monoxide, oxygen, hydrogen, nitrogen, anesthetic gases (e.g., nitrous oxide), noble gases, drugs that are gaseous at room temperature, and mixtures thereof. Immiscible therapeutic liquid that are used to treat cancer cells include antioxidant compounds such as curcumin (turmeric) or other lipid based treatments that are insoluble in aqueous systems as well as newer techniques for cancer treatment such as boron neutron capture therapy (BNCT). In some embodiments, the shear device produces a dispersion/solution having a mean bubble size of less than about 5 μm in diameter. In some embodiments, the bubbles in the produced dispersion/solution are sub-micron in diameter. In some embodiments, the average bubble size is from about 0.1 μm to about 5 μm in diameter. In some embodiments, the shear device produces a dispersion/solution having a mean bubble size of less than 400 nm in diameter. In some embodiments, the shear device produces a dispersion/solution having a mean bubble size of less than 100 nm in diameter.

In some further embodiments, oxygen and a liquid carrier is processed in a high shear device and administered to a cancer patient in conjunction with existing chemotherapy or radiotherapy. Delivering oxygen to cancerous tumors significantly boosts the chances of recovery of the patient because slightly increasing the oxygen supply strengthens blood vessels in cancer cells, making chemotherapy or radiotherapy more effective. (Cells which are damaged and weak have constricted oxygen supply and are less sensitive to existing treatments.) In some embodiments, the method disclosed herein is used to treat cancers in their later stages or cancers that have metastasized.

In some embodiments, the method promotes cancer treatment by converting therapeutic gases and/or immiscible therapeutic liquids to a form whereby they may be transported and react with and destroy cancerous cells. Passing organic containing compounds through the high shear device creates free radical charges that enable cancer treatments to selectively attack cancer tumors and cells. Any gaseous or liquid cancer therapeutics may be placed through the shear device resulting in free radical formation and charged treatment that selectively attacks cancer cells.

Arthritis and Joint Pain Treatment.

In an embodiment, a therapeutic gas or immiscible therapeutic liquid is processed in a shear device as described herein to treat arthritic conditions and/or joint pain in a patient.

Inflammation is a protective physiological reaction of vascularized tissue to local injury or tissue destruction. In its broadest sense, inflammation is the host response to tissue injury to remove injurious stimuli and initiate a healing process. It is a complex network of coordinated cellular responses designed to destroy, dilute or 'wall-off' both the noxious stimuli and the injured tissue. Types of chronic inflammation include some of the most common and debilitating human diseases, such as rheumatoid arthritis. Consequently, pharmacological agents to treat these disorders represent a tremendous interest in the global chemical and pharmaceutical industries.

Rheumatoid arthritis (RA) is known as the most common form of chronic inflammatory joint disease. RA is characterized by diffuse cartilage loss and the erosion of bone and cartilage. This process is believed to start in the synovial membrane with initial edema and hyperplasia of the synovial lining.

Without wishing to be limited by a theory, when the produced dispersion/solution (or therapeutic fluid) is introduced into a patient, sulfur-based gas (e.g., $H_2S$) nanobubbles or dispersed nano sized immiscible therapeutic liquid contained therein, gas bubbles and carrier liquid dispersion/solution may be used as an endogenous mediator of inflammation. It has been discovered that primary human articular chondrocytes (HAC) and mesenchymal progenitor cells (MPC) could synthesize $H_2S$ gas in response to pro-inflammatory cytokines relevant to human arthropathies and to determine the cellular responses to endogenous and pharmacological $H_2S$.

In some embodiments, the shear device produces a dispersion/solution having a mean gas bubble size of less than about 5 μm in diameter. In some embodiments, the bubbles in the produced dispersion/solution are sub-micron in diameter. In some embodiments, the average bubble size is from about 0.1 μm to about 5 μm in diameter. In some embodiments, the shear device produces a dispersion/solution having a mean bubble size of less than 400 nm in diameter. In some embodiments, the shear device produces a dispersion/solution having a mean bubble size of less than 100 nm in diameter.

Memory Improvement.

In an embodiment, a therapeutic gas or immiscible therapeutic liquid processed in a shear device and administered to a patient as described herein improves memory.

Erectile Dysfunction Treatment.

In an embodiment, a therapeutic gas or immiscible therapeutic liquid is processed in a shear device as described herein to treat erectile dysfunction in a patient. Without wishing to be limited by a theory, sulfur-based gas nanobubbles or dispersed nano sized immiscible therapeutic liquid contained therein, may act as a gaseous transmitter involved in the control of vascular homeostasis.

The gas bubbles may relax human and animal tissues in vitro, and may also increase intracavernous pressure. Studies have demonstrated that endogenous $H_2S$ is involved in the physiological control of penile tone. In humans, both CBS and CSE are widely expressed on trabecular muscle, implying that the smooth muscle component is the major source of $H(2)S$. Thus, the use of dispersed $H_2S$ gas may represent a promising target for development of new therapeutics for erectile dysfunction.

Incorporation of Nanodiamonds.

In some other embodiments, a therapeutic agent, nanodiamonds, and a liquid carrier are processed in a high shear device as described herein to produce a dispersion/solution and the dispersion/solution is administered to a patient intravenously. In some cases, nanodiamonds help the therapeutic agent (e.g., doxorubicin) get inside the normally chemo-resistant tumor cells and destroy such tumor cells.

Anesthesia.

In an embodiment, a gaseous anesthetic compound (anesthetic gas) is processed in a shear device as described herein to anesthetize a patient. Without wishing to be limited by a theory, when the produced dispersion/solution (or therapeutic fluid) is introduced into a patient, the gas nano bubbles or dispersed nano sized immiscible therapeutic liquid of the anesthetic compound contained therein are able to cause desired anesthetic effects in the patient. Such a method is especially useful for incorporating gaseous anesthetics that are insoluble or have low solubility into a liquid phase to form a dispersion/solution and be introduced into a patient. Suitable anesthetic gases include ethylene (solubility 0.015 g/100 ml water at 20° C.), cyclopropane (solubility 537 ppm in water at 21° C.), divinyl ether (0.0749 moles/L water at 37° C.), ethylchloride (solubility 0.678% by weight in water at 21° C.), and trichloroethylene (solubility 0.1 g/100 ml water at 20° C.), and chloroethane (solubility 0.0078 moles/L water at 20° C.).

Gene Mutation Treatment.

In an embodiment, a therapeutic gas or immiscible therapeutic liquid is processed in a shear device as described herein to react with cells that have gene mutations and render the mutation inactive by blocking the active mutation site(s). In some cases, gene mutation is caused by oxidation, and hydrogen is utilized to reverse such effects. In some further cases, a combination of therapeutic gases is used. In some instances the effect is described as reverse mutation that results from true reversion or suppression. Through the mechanism of reversion or suppression on the cellular level, the method disclosed herein is able to treat a variety of diseases, e.g., cancer. Furthermore, such a method is also able to prevent or slow down the process of aging.

Nuclear Radiation Treatment.

In an embodiment, a therapeutic gas or immiscible liquid is processed in a shear device as described herein for nuclear radiation treatment in a patient. In some cases, the therapeutic gas used is hydrogen. For example, cosmic radiation is known to induce DNA and lipid damage associated with increased oxidative stress. Hydrogen, having potent antioxidant and anti-inflammatory activities, is able to provide preventative and/or therapeutic effects toward radiation-induced adverse events. In some other cases, the therapeutic gas used is hydrogen sulfide. Hydrogen gas (H2) has antioxidant and antiapoptotic activities that protect the brain against ischemia-reperfusion injury and stroke by selectively reducing hydroxyl and peroxynitrite radicals. It is also well known that more than a half of the ionizing radiation-induced cellular damage is caused by hydroxyl radicals. Reducing hydroxyl radicals can significantly improve the protection of cells from radiation damage. In like manner hydrogen therapy may be an effective, specific and unique treatment for acute radiation syndrome.

In some embodiments, a combination of oxygen and hydrogen is utilized by first processing oxygen in the high shear device and delivering the dispersion/solution comprising oxygen nanobubbles to a patient and then processing and delivering hydrogen. In some embodiments, the liquid carrier comprises TPN, which is able to carry and deliver a larger amount of free radicals produced by high shear action.

In some embodiments the immiscible liquid is a chelating agent that chelates the radioactive element that can be excreted renally or through other techniques. Known chelating agents include diethylene triamine pentaacetic acid (DTPA), Dementia.

In an embodiment, a therapeutic gas is processed in a shear device as described herein to treat dementia in a patient. In some embodiments, hydrogen sulfide is utilized to treat Alzheimer's Disease (AD). Amyloids (both insoluble and soluble) are believed to cause various neurodegenerative diseases. Without wishing to be limited by a theory, $H_2S$ free radicals in the dispersion/solution produced under high shear action are able to destroy amyloids, especially the small, free-floating pieces of proteins (soluble amyloids) in the cerebrospinal fluid (CSF). As discussed earlier, the method disclosed herein is able to deliver the therapeutic gases across the BBB. In some other embodiments, the disclosed method is able to destroy amyloids in the liver, which may later cause brain plaques associated with AD.

Other Diseases.

In some embodiments, the method disclosed herein is able to restore rectal function. In some embodiments, the method disclosed herein is able to treat heart diseases. In some embodiments, the method disclosed herein is able to treat stroke. In some embodiments, the method disclosed herein is able to treat coma. In some embodiments, the method disclosed herein is able to treat diabetes. In some embodiments, the method disclosed herein is able to treat Parkinson's Disease (PD). It is believed that the method as described herein is able to treat a wide range of disorders.

In some embodiments, the method disclosed herein is able to treat thrombosis (blood clotting, obstructing the flow of blood inside a blood vessel). In some embodiments, the method disclosed herein is able to reduce symptoms of varicose veins.

In some embodiments, the method disclosed herein is able to treat vegetative state. In some embodiments, the method disclosed herein is able to treat paralysis. In some embodiments, the method disclosed herein is able to treat kidney diseases. In some embodiments, the method disclosed herein is able to treat viral diseases.

In some embodiments, the method disclosed herein is able to clean the blood vessels of plaques. In some embodiments, the method disclosed herein is able to treat a tropical disease. Gas or mixed gas may be used to treat or clean plague from arteries or blood vessels, as well treat tropical diseases where mobility is lost as a consequence of vessels getting plugged.

In some cases, the tropical disease is Chagas disease, which is also called American trypanosomiasis. In some cases, the tropical disease is Dengue. In some cases, the tropical disease is Helminths. In some cases, the tropical disease is African trypanosomiasis or sleeping sickness, a parasitic disease, caused by protozoa called trypansomes. In some cases, the tropical disease is Leishmaniasis, caused by protozoan parasites of the genus *Leishmania*, and transmitted by the bite of certain species of sand fly.

In some cases, the tropical disease is Leprosy or Hansen's disease, which is a chronic infectious disease caused by *Mycobacterium leprae*. In some cases, the tropical disease is Lymphatic filariasis, which is a parasitic disease caused by thread-like parasitic filarial worms called nematode worms, all transmitted by mosquitoes.

In some cases, the tropical disease is Malaria, caused by a Protozoan parasites transmitted by female *Anopheles* mosquitoes. In some cases, the tropical disease is Onchocerciasis or river blindness, which is the world's second leading infectious cause of blindness. It is caused by *Onchocerca volvulus*, a parasitic worm. It is transmitted through the bite of a black fly. In some cases, the tropical disease is Schistosomiasis, also known as schisto or snail fever, which is a parasitic disease caused by several species of flatworm in areas with freshwater snails, which may carry the parasite. In some cases, the tropical disease is Tuberculosis.

Combination Therapy.

The combination of therapeutic gases and/or liquids as discussed herein may be applied by processing a combination of gases and/or liquids (e.g., hydrogen and hydrogen sulfide) in the high shear device at the same time and then administering the produced dispersion to a patient. The combination of therapeutic gases and/or liquids as discussed herein may also be applied by processing one gas or liquid of the combination in the high shear device at a time, administering the dispersion of said gas to a patient and repeating this process with the second gas or liquid at another time that is suitable. In various embodiments, the liquid carrier comprises a total parenteral nutrition (TPN) solution. In other embodiments, the liquid carrier comprises an enhancer for carrying said therapeutic gas or liquid. TPN and/or the enhancer is able to strengthen the therapeutic effects of the combination therapy.

In some embodiments, the method of this disclosure is combined with dialysis to treat patients with kidney diseases. In principle, this method may be combined with various existing treatment regimes to enhance the treatment effects, e.g., improvement of drug efficacies.

While preferred embodiments of the invention have been shown and described, modifications thereof can be made by one skilled in the art without departing from the spirit and teachings of the invention. The embodiments described herein are some only, and are not intended to be limiting. Many variations and modifications of the invention disclosed herein are possible and are within the scope of the invention. Where numerical ranges or limitations are expressly stated, such express ranges or limitations should be understood to include iterative ranges or limitations of like magnitude falling within the expressly stated ranges or limitations (e.g., from about 1 to about 10 includes, 2, 3, 4, etc.; greater than 0.10 includes 0.11, 0.12, 0.13, and so forth). Use of the term "optionally" with respect to any element of a claim is intended to mean that the subject element is required, or alternatively, is not required. Both alternatives are intended to be within the scope of the claim. Use of broader terms such as comprises, includes, having, etc. should be understood to provide support for narrower terms such as consisting of, consisting essentially of, comprised substantially of, and the like.

Accordingly, the scope of protection is not limited by the description set out above but is only limited by the claims which follow, that scope including all equivalents of the subject matter of the claims. Each and every claim is incorporated into the specification as an embodiment of the present invention. Thus, the claims are a further description and are an addition to the preferred embodiments of the present invention. The disclosures of all patents, patent applications, and publications cited herein are hereby incorporated by reference, to the extent they provide some, procedural or other details supplementary to those set forth herein.

What is claimed is:

1. A method comprising
   mixing a therapeutic gas or a therapeutic liquid or a combination thereof and a liquid carrier in a high shear device to produce a therapeutic fluid, wherein said therapeutic fluid is a solution, a dispersion, or combination thereof containing the therapeutic gas, therapeutic liquid, or combination thereof in sub-nano size, and wherein the high shear device comprises at least one rotor and at least one complementarily-shaped stator; and
   administering the produced therapeutic fluid intravenously to a patient;
   wherein the therapeutic fluid is supersaturated with the therapeutic gas, the therapeutic liquid, or combination thereof.

2. The method of claim 1 wherein said therapeutic fluid is no less than 5% supersaturated.

3. The method of claim 1 wherein said therapeutic gas is selected from the group consisting of ozone, sulfur based gases, carbon monoxide, oxygen, hydrogen, nitrogen, an anesthetic gas, a noble gas, and mixtures thereof.

4. The method of claim 1 wherein said therapeutic liquid is selected from the group consisting of sulfur, a sulfate, an organo metallic, an antibiotic, a steroid, a vitamin, an organosulfur compound, allyl propyl disulfide, diallyl disulfide (DADS or 4,5-dithia-1,7-octadiene), allyl trisulfide (DATS), S-Allyl cysteine (SAC), a vinyldithiine, a sulfonyl compound, an antioxidant, a lipid, a chelating agent, and combinations thereof.

5. The method of claim 4 wherein said antioxidant comprises curcumin (turmeric); wherein said chelating agent comprises diethylene triamine pentaacetic acid (DTPA); wherein said vinyldithiine comprises 2-vinyl-[4H]-1,3-dithiine or 3-vinyl-[4H]-1,2-dithiine; wherein said organosulfur compound comprises allicin; and wherein said sulfonyl compound comprises ajoene.

6. The method of claim 1 wherein the therapeutic gas comprises hydrogen or hydrogen sulfide or oxygen.

7. The method of claim 1 wherein the therapeutic gas is oxygen and the produced therapeutic fluid is utilized in conjunction with a blood substitute.

8. The method of claim 1 wherein a combination of therapeutic gases or a combination of therapeutic liquids or a combination of therapeutic gas and liquid is utilized.

9. The method of claim 1 wherein said liquid carrier comprises a total parenteral nutrition (TPN) solution.

10. The method of claim 1 wherein said liquid carrier comprises an enhancer for carrying said therapeutic gas or said therapeutic liquid.

11. The method of claim 1 further comprising incorporating a medicine into the produced therapeutic fluid prior to administering the therapeutic fluid to the patient.

* * * * *